US00PP11016P

United States Patent [19]

Zary

[11] Patent Number: Plant 11,016

[45] Date of Patent: Jul. 27, 1999

[54] GRANDIFLORA ROSE PLANT NAMED 'JACCINQO'

[75] Inventor: Keith W. Zary, Thousand Oaks, Calif.

[73] Assignee: Bear Creek Gardens, Inc., Medford, Oreg.

[21] Appl. No.: 09/028,280

[22] Filed: Feb. 24, 1998

[51] Int. Cl.[6] ..... A01H 5/00

[52] U.S. Cl. ..... Plt./136

[58] Field of Search ..... Plt./136, 135, 139

[56] References Cited

U.S. PATENT DOCUMENTS

P.P. 5,120 10/1983 Warriner ..... Plt./136

*Primary Examiner*—Howard J. Locker

*Attorney, Agent, or Firm*—Klarquist Sparkman Campbell Leigh & Whinston, LLP

[57] ABSTRACT

Grandiflora rose plant having orange to orange-coral flowers presented in large, open clusters; dark green, glossy foliage; dense, well branched plant habit; and resistance to powdery mildew and rust.

1 Drawing Sheet

The present invention relates to a new and distinct variety of rose plant of the grandiflora class which was originated by me by crossing the variety 'JACient,' U.S. Plant Pat. No. 6,725, with an unnamed seedling.

The primary objective of this breeding was to produce a new rose variety having the dense, well branched habit, dark green foliage and open flower clusters of the female parent combined with the bright orange flowers and disease resistance of the male parent. The objective was substantially achieved, along with other desirable improvements, as evidenced by the following unique combination of characteristics that are outstanding in the new variety and that distinguish it from its parents, as well as from all other varieties of which I am aware:

1. Orange to coral-orange flowers presented in large, open clusters;
2. Dark green, glossy foliage;
3. Dense, well branched plant habit;
4. Resistance to powdery mildew and rust.

Asexual reproduction of this new variety by budding, as performed at Somis, Calif. shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—'JACient', U.S. Plant Pat. No. 6,725.

*Pollen parent.*—Unnamed seedling (unpatented).

Classification:

*Botanical.*—Rosa hybrida.

*Commercial.*—Grandiflora.

FLOWER

Observations made from specimens grown in a garden environment at Somis, Calif., from January 1996 to December 1997.

Blooming habit: Recurrent.

Bud:

*Size.*—1½" long when the petals start to unfurl.

*Form.*—Long, pointed ovoid.

*Color.*—When sepals first divide, bud color is Red Group 44A. When half blown, the upper sides of the petals are Red Group 44C, the lower sides of the petals are Red Group 47B.

*Sepals.*—Color: Green Group 138B. Surface texture: Covered in fine hairs. There are three normally to heavily appendaged sepals. There are two unappendaged sepals.

*Receptacle.*—Color: Green Group 147B. Shape: Funnel. Size: Medium (⅜"×5/16"). Surface: Smooth.

*Peduncle.*—Length: Medium (3" to 3½"). Surface: Glandular. Color: Medium green. Strength: Stiff, erect.

Bloom:

*Size.*—Medium. Average open size is 3½" to 4".

*Borne.*—Several together in clusters of 3 to 5 blooms having rounded shape.

*Stems.*—Medium (14–18"), strong.

*Form.*—When first open: High centered. Permanence: Flattens outer petal edges curl slightly.

*Petalage.*—Number of petals under normal conditions: 20–25.

*Color.*—The upper sides of the petals are Red Group 44C. The reverse sides of the petals are Red Group 47C. The base of each petal has a small (⅜"×⅜") Yellow Group 7D spot at the point of attachment. The major color on the upper sides is Red Group 44C.

*Variegations.*—Occasional greenish-white streak on the guard petals.

*Discoloration.*—No change through day seven or eight when there is petal drop.

*Fragrance.*—Slight.

Petals:

*Texture.*—Thick.

*Shape.*—Deltoid.

*Form.*—Tips slightly recurved.

*Arrangement.*—Imbricated. Petaloids in the center: Few, small.

*Persistence.*—Petals drop off cleanly before drying.

*Lastingness.*—On the plant: Long (7–8 days). As a cut flower: Long (10 days).

Reproductive parts:

*Anthers.*—Size: Medium. Quantity: Many. Color: Yellow. Arrangement: Regular around styles.

*Filaments.*—Color: Yellow.
*Pollen.*—Color: Gold yellow.
*Styles.*—Color: Red.
*Stigmas.*—Color: Greenish white.

Plant:
*Form.*—Bush.
*Growth.*—Vigorous; upright; branching. At maturity, height is five feet, width is four feet.

Foliage: Number of leaflets on normal mid-stem leaves: Five.
*Size.*—Large (5½" to 6"×4–4½").
*Quantity.*—Abundant.
*Color.*—New foliage: Upper and lower sides: Greyed-Red Group 178A. Old foliage: Upper side: Green Group 139A. Lower Side: Yellow Green Group 147C.

Leaflets:
*Shape.*—Pointed oval.
*Texture.*—Upper side: Leathery, glossy.
*Edge.*—Serrated.
*Serration.*—Single, small.
*Petiole rachis.*—Color: Green.
*Petiole underside.*—Smooth.
*Stipules.*—Medium (9/16"), serrated.
*Disease resistance.*—Resistant to mildew and rust under normal growing conditions at Somis, Calif.

Wood:
*New wood.*—Color: Reddish. Bark: Smooth.
*Old wood.*—Color: Green. Bark: Smooth.

Prickles:
*Quantity.*—On main canes from base: Ordinary. On laterals from main canes: Ordinary.
*Form.*—Hooked downward.
*Color when young.*—Greyed-Purple Group 183A.

Small prickles:
*Quantity.*—On main stalks: None. On laterals: Few.
*Color.*—Greyed-Orange Group 177A.

I claim:

1. A new and distinct variety of rose plant of the grandiflora class, as herein shown and described, characterized particularly by its orange to orange-coral flowers presented in large, open clusters; dark green, glossy foliage; dense, well branched plant habit; and resistance to powdery mildew and rust.

* * * * *

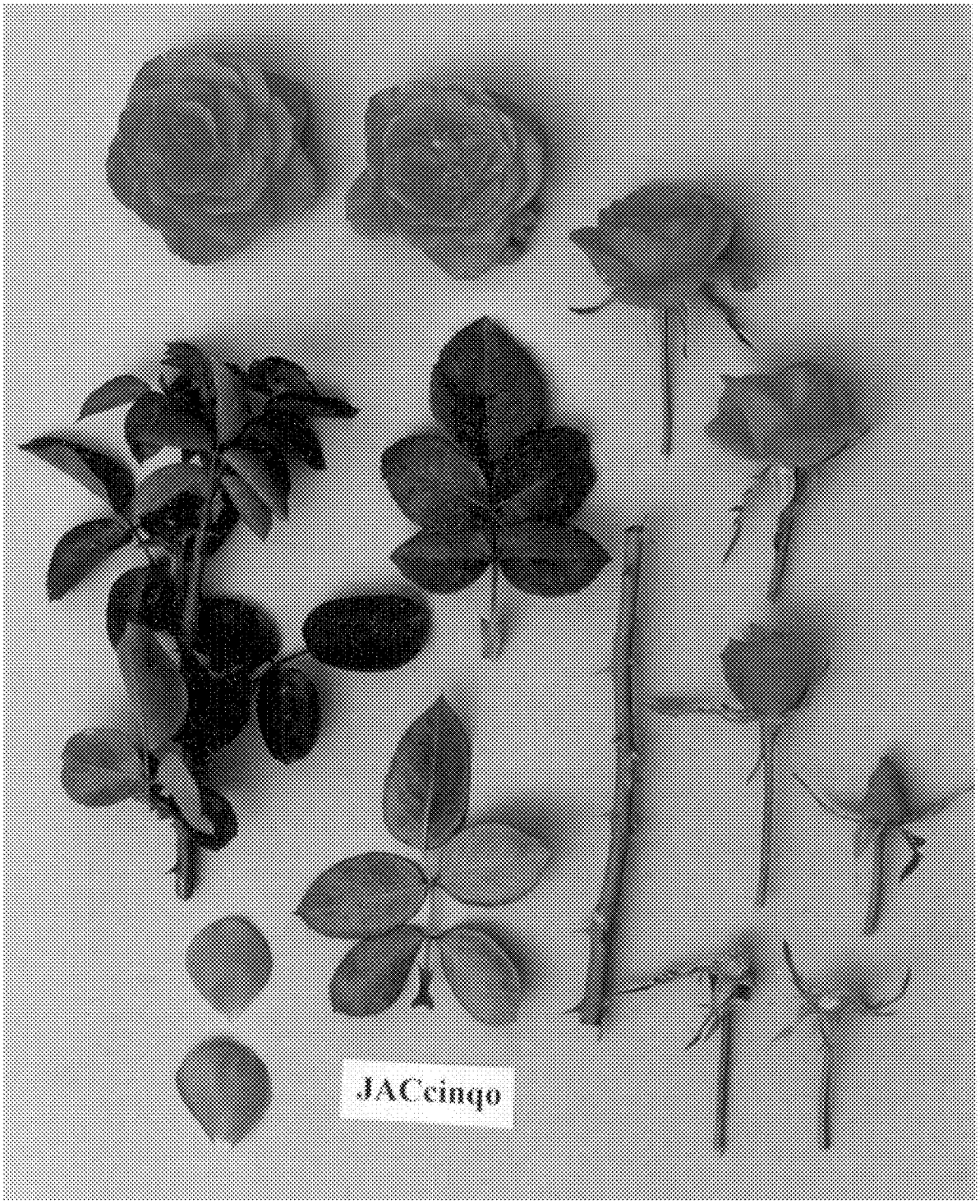
JACcinqo